US00PP15591P2

(12) United States Plant Patent
Heemskerk

(10) Patent No.: US PP15,591 P2
(45) Date of Patent: Feb. 22, 2005

(54) ***HOSTA* PLANT NAMED 'LADY GUINEVERRE'**

(50) Latin Name: *Hosta hybrid*
Varietal Denomination: Lady Guineverre

(76) Inventor: Gerardus Heemskerk, De Boender 7, Noordwijk 2204 AE (NL)

( * ) Notice: Subject to any disclaimer, the term of this patent is extended or adjusted under 35 U.S.C. 154(b) by 21 days.

(21) Appl. No.: 10/760,931

(22) Filed: Jan. 20, 2004

(51) Int. Cl.[7] ..... A01H 5/00

(52) U.S. Cl. ..... Plt./353

(58) Field of Search ..... Plt./353

*Primary Examiner*—Kent Bell
*Assistant Examiner*—Louanne Krawczewicz Myers
(74) *Attorney, Agent, or Firm*—Mark P. Bourgeois

(57) ABSTRACT

A new cultivar of *Hosta* plant named 'Lady Guineverre' that is characterized in having variegated foliage and a large number of flowers. The leaves of 'Lady Guineverre' have wide yellow-green centers with narrow dark green margins. In combination, these traits set 'Lady Guineverre' apart from other varieties of *Hosta* known to the inventor.

2 Drawing Sheets

Botanical classification: *Hosta* hybrid.
Variety denomination: 'Lady Guineverre'.

BACKGROUND OF THE INVENTION

The present invention relates to a new and distinct cultivar of plaintain lily that is grown for its thick, furrowed, variegated leaves. The new cultivar is known botanically as *Hosta* and will be referred to hereinafter by the cultivar name 'Lady Guineverre'.

'Lady Guineverre' was discovered by the inventor in a cultivated area of Noordwijk, Netherlands in 1996 as a naturally occurring branch sport of the parent plant *Hosta* 'Elizabeth' (not patented). 'Lady Guineverre' was selected, by the inventor, for its unique variegated leaves with dark green margins and yellow-green centers.

The plant most similar to 'Lady Guineverre' is the parent plant *Hosta* 'Elizabeth'. 'Lady Guineverre' differs from 'Elizabeth' in its variegated foliage and number of flowers. The leaves of 'Lady Guineverre' have wide yellow-green centers with narrow dark green margins. The leaves of 'Elizabeth' are all green. 'Lady Guineverre' also flowers more prolifically than the parent plant 'Elizabeth'.

Asexual reproduction of the new cultivar was first accomplished in a cultivated area of Roelofarendsueen, Netherlands in 1997 using tissue culture. The characteristics of the new cultivar have been determined stable and are reproduced true to type in successive generations.

SUMMARY OF THE INVENTION

The following traits have been repeatedly observed and represent the characteristics of 'Lady Guineverre'. These traits in combination distinguish the new cultivar from other varieties known to the inventor. 'Lady Guineverre' has not been tested under all possible conditions and phenotypic differences may be observed with variations in environmental, climatic and cultural conditions.

1. *Hosta* 'Lady Guineverre' exhibits large, furrowed leaves.
2. *Hosta* 'Lady Guineverre' has a larger quantity of flowers than the parent plant.

3. *Hosta* 'Lady Guineverre' exhibits leaves with narrow dark green margins and wide yellow-green centers.
4. *Hosta* 'Lady Guineverre' exhibits purple flowers.

BRIEF DESCRIPTION OF THE DRAWINGS

The accompanying color photographs illustrate the distinguishing traits of 'Lady Guineverre'.

The photograph on Sheet 1 shows a side view of the entire plant.

The photograph on top of Sheet 2 shows a close up of the flowers.

The photograph on bottom of Sheet 2 illustrates the yellow-green center and dark green margins on a leaf.

All photographs were taken in Noordwijk, Netherlands of field grown plants.

All photographs have been made using conventional techniques and although colors may appear different from actual colors due to light reflectance they are as accurate as possible by conventional photography.

BOTANICAL DESCRIPTION OF THE PLANT

The following is a detailed description of 1 year old field grown plants of the new cultivar. Daytime growing temperatures were from 15 to 30° Centigrade. Nightime growing temperatures were from 7 to 18° Centigrade. Data was recorded in Noordwijk, Netherlands. The color determinations are in accordance with the 2001 R.H.S. Color Chart of The Royal Horticultural Society, London, England, except where general color terms of ordinary dictionary significance are used. Growing conditions are similar to other *Hosta* varieties.

Botanical classification: *Hosta* hybrid 'Lady Guineverre'.
Commercial classification: Herbaceous perennial.
Common name: Plaintain lily.
Use: Container or landscape plant.
Cultural requirements: Plant in full shade or part shade, and plant in organically enriched soil.
Parentage: *Hosta* 'Lady Guineverre' is a naturally occurring branch sport of *Hosta* 'Elizabeth'.

Plant description:

*Plant habit.*—Broad upright.
*Vigor.*—Moderate.
*Growth rate.*—Flowering stems grow at a rate of 20 cm. per month.
*Plant shape.*—Broad inverted triangle.
*Height.*—78 cm. in height including flowers, 24 cm. not including flowers.
*Width.*—52 cm. in width.
*Hardiness.*—USDA Zones 4–8.
*Propagation.*—Tissue culture.
*Time to initiate roots.*—1 week at 15° Centigrade.
*Crop time.*—Approximately 15 weeks.

Branching habit: Basal rosette with flowering stems developing from the rosette.

Foliage:

*Compound or single.*—Single.
*Quantity.*—Approximately 23 per rosette.
*Durability of foliage to stress.*—Moderate to high.
*Shape.*—Ovate to elliptical.
*Division.*—Simple.
*Apex.*—Long apiculate.
*Base.*—Acuminate.
*Venation.*—Camptodrome.
*Vein color upper surface.*—In yellow-green areas the veins are 151D and in the margins between 139A and 147A.
*Vein color lower surface.*—In yellow-green areas the veins are 145B and in the margins 137A.
*Margins.*—Entire, wavy.
*Surface.*—Dull and furrowed.
*Pubescence.*—Absent.
*Arrangement.*—Alternate in basal rosette.
*Attachment.*—Petiolate.
*Petiole dimensions.*—1 cm. in width and 22.7 cm. in length.
*Petiole shape.*—V-shaped in cross section.
*Petiole color upper side.*—144A to 144B, margins 137B.
*Petiole color under side.*—145B to 145D, margins 143A.
*Leaf dimensions.*—18.1 cm. in length and 7.5 cm. in width.
*Leaf color on young plants upper surface.*—144B with irregular margins 143B on upper half of leaf.
*Leaf color on young plants under surface.*—Between 144B and 146D with irregular margins 144A on upper half of leaf.
*Leaf color on mature plants upper surface.*—151D with irregular margins varying between 139A and 147A.
*Leaf color on mature plants under surface.*—145B with irregular margins 137A.
*Fragrance.*—Absent.

Flowers:

*Shape.*—Campanulate.
*Type of inflorescence.*—Raceme.
*Inflorescence dimensions.*—26 cm. in height and 8.3 cm. in width.
*Quantity of flowers per inflorescence.*—Approximately 16 flowers per inflorescence.
*Quantity of flowers per lateral stem.*—Approximately 16 flowers per lateral stem.
*Quantity of flowers per plant.*—Approximately 32.
*Persistent or self-cleaning.*—Self-cleaning.
*Aspect.*—Facing outward and slightly pendulous.
*Bloom period.*—Blooms from late June to September.
*Fragrance.*—None.
*Bud dimensions.*—4.8 cm. in length and 1.0 cm. in diameter.
*Bud shape.*—Narrow obovate.
*Bud color.*—76A with violet stripes 84A.
*Flower longevity.*—7 days.
*Flower dimensions.*—3.5 cm. in diameter and 5.7 cm. in height.
*Rate of opening (per flowering stem).*—10% open all at once.
*Tepals.*—Six in number.
*Tepal shape.*—Oblanceolate.
*Tepal apex.*—Acute.
*Tepals fused or unfused.*—Base fused and upper 30% of tepals are free.
*Tepal margin.*—Entire.
*Tepal surface.*—Dull and glabrous.
*Tepal dimensions.*—5.5 cm. in length and 8 mm. in width.
*Tepal color when opening upper side.*—76C with darker base, 76A and veins, 76A.
*Tepal color when opening under side.*—76B with darker base, 76A and veins, 76A.
*Tepal color fully opened upper side.*—76C with darker base, 76A and veins, 76A.
*Tepal color fully opened under side.*—76B with darker base, 76A and veins, 76A.
*Petaloids.*—None.
*Sepals.*—No separate sepals, only tepals.
*Peduncle dimensions.*—40.6 cm. in length and 3 mm in diameter.
*Peduncle color.*—144A with grey-purple dots 187B.
*Peduncle strength.*—Strong.
*Peduncle angle.*—80°.
*Pedicel.*—Present.
*Pedicel strength.*—Strong.
*Pedicel dimensions.*—1.5 mm. in diameter and 1.1 cm. in length.
*Pedicel angle.*—40°.
*Pedicel color.*—147B.
*Bract.*—One at the base of each pedicel.
*Bract dimensions.*—3 cm. in length and 1.1 cm in width.
*Bract color.*—146B.
*Bract shape.*—Ovate.
*Bract apex.*—Acute.
*Bract base.*—Cuneate.

Reproductive organs:

*Stamens.*—Six in number.
*Anther color.*—18A.
*Amount of pollen.*—Low.
*Pollen color.*—9A.
*Anther shape.*—Oblong.
*Anther attachment.*—Dorsifixed.
*Filament dimensions.*—5.2 cm in length.
*Filament color.*—155A.
*Pistil.*—One in number.
*Pistil dimensions.*—5.8 cm. in length and 1 mm. in diameter.
*Stigma shape.*—Crested.
*Stigma color.*—155C.
*Style color.*—155C at the top, 155A in the middle, 145B at the base.
*Style dimensions.*—5.75 cm. in length and 1 mm. in diameter.
*Ovary color.*—144B.

Seed production: Has not been observed.

Disease resistance: Has not been observed.

It is claimed:

1. A new and distinct cultivar of *Hosta* plant named 'Lady Guineverre' as herein described and illustrated.

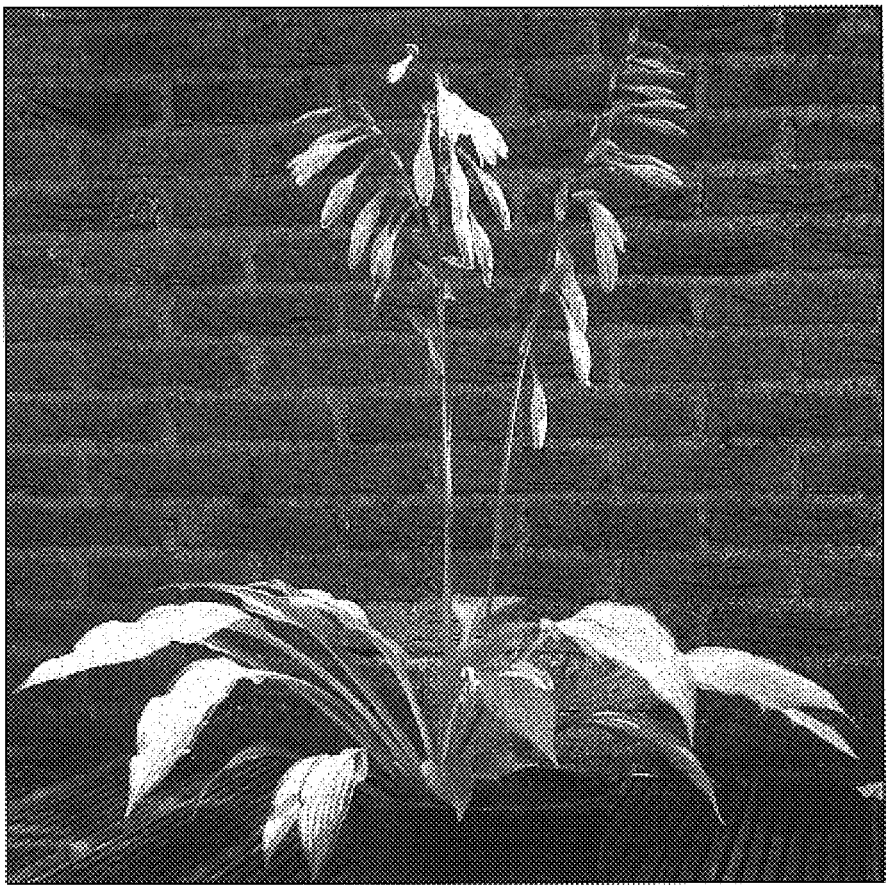

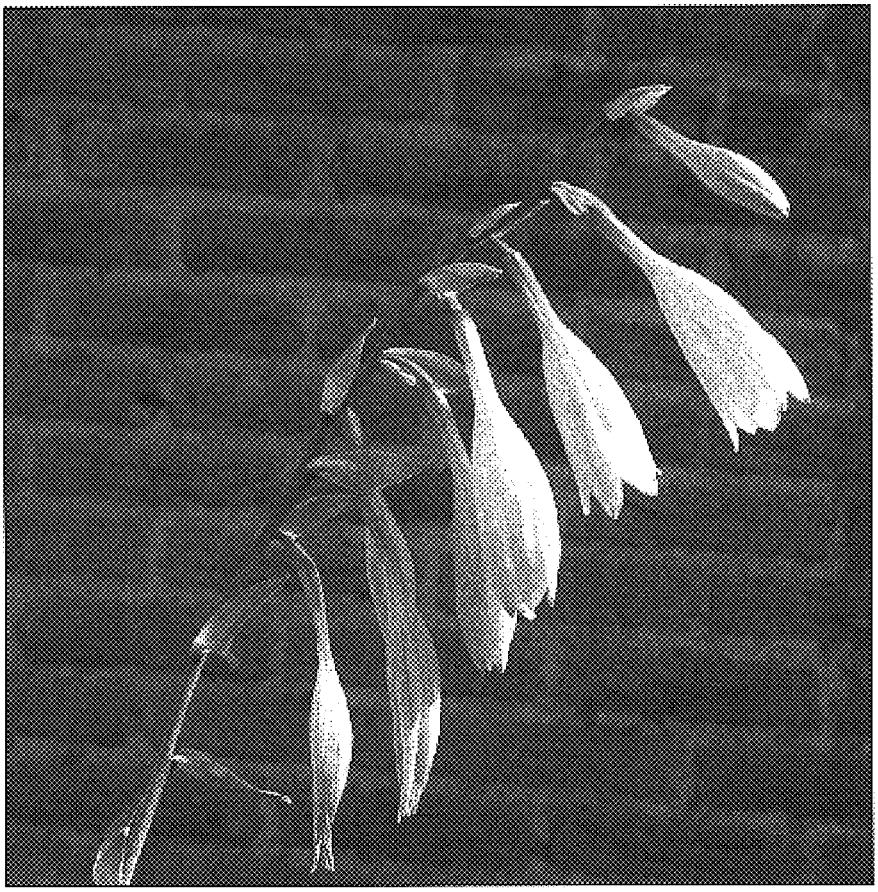
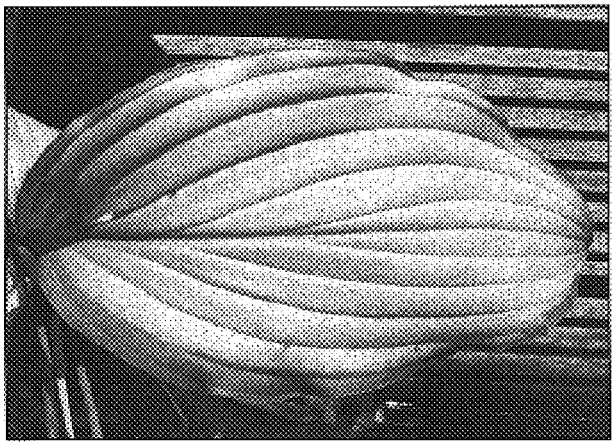

* * * * *